(12) United States Patent
Roh et al.

(10) Patent No.: US 9,173,786 B2
(45) Date of Patent: Nov. 3, 2015

(54) ABSORBENT PERSONAL CARE ARTICLE HAVING WINGS AND PROTECTIVE STRIPS

(71) Applicant: Kimberly-Clark Worldwide, Inc.

(72) Inventors: SeongDae Roh, Yongin-si (KR); HyongBom Kim, YongIn-Si (KR); HyungWoo Park, SuWon-Si (KR); SeoYeon Son, SeongNam-Si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 233 days.

(21) Appl. No.: 13/897,747

(22) Filed: May 20, 2013

(65) Prior Publication Data

US 2014/0343525 A1 Nov. 20, 2014

(51) Int. Cl.
- A61F 13/15 (2006.01)
- A61F 13/56 (2006.01)
- A61F 13/476 (2006.01)
- A61F 13/475 (2006.01)

(52) U.S. Cl.
CPC ........... *A61F 13/5616* (2013.01); *A61F 13/476* (2013.01); *A61F 13/4751* (2013.01); *A61F 13/5611* (2013.01)

(58) Field of Classification Search
CPC ......................... A61F 13/5611; A61F 13/5616
USPC ............................ 604/385.28, 385.04, 385.05
See application file for complete search history.

(56) References Cited

U.S. PATENT DOCUMENTS

| | | |
|---|---|---|
| 4,059,114 A | 11/1977 | Richards |
| 4,589,876 A | 5/1986 | Van Tilburg |
| 4,781,710 A | 11/1988 | Megison et al. |
| 4,862,574 A | 9/1989 | Seidy |
| 5,342,647 A | 8/1994 | Heindel et al. |
| 5,387,210 A | 2/1995 | Murakami |
| 5,391,162 A | 2/1995 | Widlund et al. |
| 5,401,268 A | 3/1995 | Rodier |
| 5,415,640 A | 5/1995 | Kirby et al. |
| 5,447,507 A | 9/1995 | Yamamoto |
| 5,542,941 A | 8/1996 | Morita |
| 5,558,657 A | 9/1996 | Hammons et al. |
| 5,584,829 A | 12/1996 | Lavash et al. |
| 5,591,147 A | 1/1997 | Couture-Dorschner et al. |
| 5,618,283 A | 4/1997 | Yamamoto |
| 5,649,917 A | 7/1997 | Roberts et al. |
| 5,681,303 A | 10/1997 | Mills et al. |

(Continued)

FOREIGN PATENT DOCUMENTS

| | | |
|---|---|---|
| EP | 0511905 B1 | 8/1995 |
| EP | 0769284 A1 | 4/1997 |

(Continued)

*Primary Examiner* — Jacqueline Stephens

(74) *Attorney, Agent, or Firm* — Kimberly-Clark Worldwide, Inc.

(57) ABSTRACT

An absorbent personal care article, such as a sanitary napkin or incontinence pad is described having a longitudinal centerline and a transverse centerline and including a pair of opposed first and second wings extending along the longitudinal sides of the article. The article further includes first and second protective strips attached to the sides of the article such that when the wings are folded under the article and around the wearer's undergarment, the first and second protective strips extend laterally outboard of the article and the edges of the wearer's undergarment to provide additional protection against leakage of body fluids deposited onto the absorbent personal care article.

18 Claims, 7 Drawing Sheets

(56) References Cited

U.S. PATENT DOCUMENTS

| | | |
|---|---|---|
| 5,704,928 A | 1/1998 | Morita et al. |
| 5,772,650 A | 6/1998 | Mizutani |
| 5,921,975 A | 7/1999 | Suzuki et al. |
| 5,922,165 A | 7/1999 | Bitowft et al. |
| 5,961,505 A | 10/1999 | Coe et al. |
| 6,117,523 A | 9/2000 | Sugahara |
| 6,328,722 B1 | 12/2001 | Lavash et al. |
| 6,387,084 B1 | 5/2002 | VanGompel et al. |
| 6,551,296 B1 | 4/2003 | Boulanger |
| 6,592,561 B2 | 7/2003 | Simard et al. |
| 6,602,236 B1 | 8/2003 | Mizutani et al. |
| 6,896,668 B2 | 5/2005 | Kashiwagi et al. |
| 6,902,552 B2 | 6/2005 | VanGompel et al. |
| 7,037,298 B2 | 5/2006 | Ohshima et al. |
| 7,063,689 B2 | 6/2006 | VanGompel et al. |
| 7,070,672 B2 | 7/2006 | Alcantara et al. |
| 7,686,790 B2 | 3/2010 | Rasmussen et al. |
| 2004/0040650 A1 | 3/2004 | Venturino et al. |
| 2004/0243087 A1 | 12/2004 | Kinoshita et al. |
| 2005/0137556 A1 | 6/2005 | Brisebois |
| 2005/0182374 A1 | 8/2005 | Zander et al. |
| 2005/0206038 A1 | 9/2005 | Brisebois et al. |
| 2006/0240136 A1 | 10/2006 | Brisebois et al. |
| 2010/0152692 A1 | 6/2010 | Ong et al. |
| 2011/0178492 A1 | 7/2011 | Coates |
| 2013/0123731 A1 | 5/2013 | Mercer et al. |

FOREIGN PATENT DOCUMENTS

| | | |
|---|---|---|
| EP | 1208823 A1 | 5/2002 |
| EP | 0994686 B1 | 11/2002 |
| EP | 0940132 B1 | 11/2003 |
| EP | 0843539 B1 | 12/2006 |
| JP | 2006-296841 A | 11/2006 |
| KR | 10-2000-0062826 A | 10/2000 |
| WO | WO 95/20931 A1 | 8/1995 |
| WO | WO 96/23472 A1 | 8/1996 |
| WO | WO 97/40804 A1 | 11/1997 |
| WO | WO 98/55063 A1 | 12/1998 |
| WO | WO 99/00095 A1 | 1/1999 |
| WO | WO 2008/29558 A1 | 3/2008 |
| WO | WO 2009/043101 A1 | 4/2009 |
| WO | WO 2011/966483 A1 | 8/2011 |
| WO | WO 2012/100970 A1 | 8/2012 |

ABSORBENT PERSONAL CARE ARTICLE HAVING WINGS AND PROTECTIVE STRIPS

FIELD OF THE INVENTION

The present invention relates to absorbent personal care articles. More particularly, it relates to absorbent personal care articles having foldable wings or flaps and protective strips affixed to the sides of the articles which work in conjunction with the wings to provide increased protection against leakage of body fluids onto undergarments or other articles of clothing.

BACKGROUND

Absorbent personal care articles such as sanitary napkins, panty liners and incontinence pads commonly utilize a pair of wings or flaps which are used to help secure the article in place to the wearer's undergarments. Generally, the wings are folded around the outside of the wearer's undergarment and either attach to the outside of the undergarment or to themselves via adhesive, mechanical fasteners or other fastening means. Once secured to the undergarment the wings help reduce the likelihood that the article will become dislodged and move out of position. Examples of such foldable wing fasteners are shown and described in U.S. Pat. No. 4,589,876 Van Tilberg; EP051190B1 Pigneul; U.S. Pat. No. 5,401,268 Rodier; and EP1208823A1 Hohmann. In addition to securing the article to the wearer's undergarment, the wings or flaps are also designed to assist in the prevention of side leakage of body exudates received by the article. Unfortunately, it has been determined that these two functions can be at odds with one another.

One advantage of wings or flaps is the sense of security they provide to the wearer of the product that the product will stay in place. As a result, the users will often tighten the wings to an excessive degree. This in turn tends to pull the wings downwardly which is counterproductive to leakage protection as it distorts the intended flat or preferably upwardly curving nature of the product to a point that the lateral side edges start to curve downwardly which then facilitates run-off of body fluids that have been deposited onto the topsheet or body-contacting surface of the product.

Conversely, if the wing tension is reduced by not wrapping the wings as tightly about the crotch region of the undergarment, leakage protection will increase but at the expense of the secure feeling the wearer achieves by a tighter wrapping procedure. One possible solution is to increase the size of the wings. While this can increase protection against leaks, it also can cause the product to become more uncomfortable to wear. Yet another solution is to increase the overall dimensions of the base product by making it longer and/or wider. This can cause the product to become more uncomfortable to wear.

There is therefore a need for an improved product design that results in a product that allows the wearer to wrap the wings about varying sizes of undergarments worn by the wearer to the desired degree to provide the security that the product will remain in place during use and not shift during periods of increased activity. At the same time, there is also the need for a product that will still provide the necessary body-contacting surface area that would normally be provided at the side margins of product despite the wings being attached in a manner that causes a downward pull on the sides of the product.

SUMMARY OF THE INVENTION

The present invention addresses problems experienced with the wing designs of the prior art by providing an absorbent personal care article including wings on either side of the product supplemented with protective strips of material that are separate from the wings so that when the wings are folded downwardly, there is still material along the sides of the product that can facilitate good fit and reduction in leakage of body exudates deposited onto and into the product.

In one embodiment the absorbent personal care article comprises an elongate shape defined by opposed first and second sides and opposed front and rear ends. The article defines a longitudinal axis, a transverse axis and a vertical axis normal to the longitudinal axis and the transverse axis. The article has a liquid permeable topsheet which defines a top surface and a bottom surface along with a liquid impermeable backsheet and an absorbent core disposed between the liquid permeable topsheet and the liquid impermeable backsheet. A first wing extends from the first side and it has a wing proximal edge and a wing distal edge. In similar fashion, the article includes a second wing extending from the second side and having a wing proximal edge and a wind distal edge. To allow the article to be secured to the undergarment of the wearer, a fastener is positioned on at least one of the first and second wings. The first wing and second wing are each respectively attached to the first side and the second side of the article and the first wing has a first hinge line and the second wing has a second hinge line. The first wing and the second wing are adapted during use to be folded along the respective first and second hinge lines downwardly relative to the vertical axis and thus towards the backsheet.

To protect against side leakage, the article further includes a first protective strip and a second protective strip each defining a proximal edge and a distal edge and a width therebetween. The first and second protective strips each define a front end portion and a rear end portion with a mid-portion disposed between the front end portion and the rear end portion. The front end portion is separated from the mid-portion by a front transition portion and the rear end portion is separated from the mid-portion by a rear transition portion. The first protective strip is located adjacent to the first side of the article and the second protective strip is located adjacent to the second side of the article such that at least a portion of the first protective strip including at least a portion of the distal edge extends beyond the first hinge line and at least a portion of the second protective strip including at least a portion of the distal edge extends beyond the second hinge line with the first and second hinge lines being located below the respective first and second protective strips relative to the vertical axis. The mid-portions of the first and second protective strips each have a distal edge in which at least a portion of the distal edge is straight with the front transition portion and the rear transition portions each having a width which is less than the width of the front end portion, the mid-portion and the rear end portion.

If desired, the absorbent personal care article can have at least one of the front end portion and the rear end portion of the first and second protective strips be non-linear. For example, they can be convex as viewed relative to the proximal edges of the protective strips but they can also have other non-straight designs or combinations of linear and non-linear designs.

To increase the stiffness of the protective strips, the first and second protective strips can be embossed or employ other stiffening means to increase the peak load stiffness of the strips.

Typically, each of the first and second protective strips will be attached to the top surface of the topsheet but the strips can also be attached to other layers or the proximal edges of the strips can be embedded between layers to secure them to the article. In other situations, the protective strips can be formed wholly or partially from other components of the absorbent article.

So as to maintain the comfort of the article, the distal edges of the front end portion and the rear end portion of the first and second protective strips do not extend beyond the respective first side and second side of the article. In so doing, the overall footprint of the article is not increased by these portions thereby maintaining the comfort and size of the article. However, in some applications it may be desirable to have these portions of the article extend beyond the periphery of the article formed by the other layers or components of the article.

To further maintain the comfort of the article, in certain embodiments it is desirable to have the width of the mid-portion of the first and second protective strips be within ten percent of the width of at least one of the front end portion and the rear end portion of the strip. In another embodiment the front and rear end portions can be the same width as the mid-portion of the strip and all three of these portions are wider than the front transition portion and the rear transition portion. To maximize protection from side leakage it is desirable that the mid-portion have a width that is greater than the width of the front end portion and the rear end portion. As a result, during use, when the article is attached to the crotch region of an undergarment by wrapping the wings around the, lateral edges of the undergarment, at least a portion of the protective strips will extend laterally beyond the lateral edges of the undergarment thereby providing extra protection against leakage of body fluids received by the article.

While the basis weight of the protective strips can be varied depending on the overall parameters for a particular design, typically the first and second protective strips will have a basis weight between about 15 and about 200 grams per square meter. It has been found, however, that by using the stiffening means described herein, the basis weight of the protective strips in some applications can be lowered as the overall stiffness can be increased by further acting upon the material forming the protective strips such as by embossing them or coating or treating them with adhesives and other materials. Another means for increasing the effective stiffness of the protective strips is to make the distal edges of the first and second protective strips stiffer than the remainder of the strips.

When the first and second protective strips are separate pieces of material, they can be attached to the article by way of an attachment zone. This attachment zone is typically inboard of the first and second hinge lines of the respective first and second protective strips.

In certain embodiments it has been found to be desirable for the proximal edges of the mid-portions of the first and second protective strips to not overlap the absorbent core.

The absorbent personal care article is designed such that the distal edges of the first and second protective strips are unattached to the article. In this regard, the entire distal edge of the protective strips can be unattached to the article or only select portions. For example, the mid-portion of the first and second protective strips are unattached to the article as this allows the wings to be folded downwardly while still allowing the mid-portion of the strips to remain in the same general plane formed by the X and Y axes of the product.

The degree of stiffness of the protective strips can be expressed in terms of their peak load stiffness in accordance with the Circular Bend test. The strips will have a peak load stiffness when compared to the wings themselves of the product which is at least about 20 percent, desirably at least about 50 percent and more desirably at least about 100 percent greater than the wings themselves. The percent increase in stiffness of the protective strips as compared to the wings themselves should range between about 20 percent and about 260 percent, desirably between about 20 and about 160 percent and more desirably between about 50 and about 160 percent. If the protective strips are made too stiff, problems can arise such as irritation to the skin of the wearer which is an undesirable attribute.

In an alternate embodiment, the absorbent personal care article can be equipped with protective strips wherein the front end portion, the rear end portion and the front and rear transition portions of the strips have been removed, thereby forming a truncated version of the protective strips. In this way, money, material and processing steps can be reduced and the protective strips have a length as measured in the longitudinal direction (axis X) which is approximately equal to the length of the wings in the longitudinal direction. In this embodiment, the article will once again have an elongate shape defined by opposed first and second sides and opposed front and rear ends with the article defining a longitudinal axis, a transverse axis and a vertical axis normal to the longitudinal axis and the transverse axis. The article will include a liquid permeable topsheet defining a top surface and a bottom surface, a liquid impermeable backsheet and an absorbent core disposed between the liquid permeable topsheet and the liquid impermeable backsheet.

A first wing extends from the first side having a wing proximal edge and a wing distal edge and a second wing extends from the second side having a wing proximal edge and a wing distal edge. A fastener is positioned on at least one of the first and second wings with the first wing and second wing each being respectively attached to the first side and the second side of the article. The first wing has a first hinge line and the second wing has a second hinge line with the first wing and the second wing being adapted during use to be folded along the respective first and second hinge lines downwardly relative to the vertical axis towards the backsheet.

In this embodiment the article includes a first protective strip and a second protective strip each defining a proximal edge and a distal edge and a width therebetween wherein at least a portion of the distal edge is straight. The first and second protective strips are each in vertical juxtaposition with the respective first wing and second wing. The first protective strip is located adjacent the first side and the second protective strip is located adjacent the second side of the article such that at least a portion of the first protective strip including at least a portion of the distal edge extends beyond the first hinge line and at least a portion of the second protective strip including at least a portion of the distal edge extends beyond the second hinge line with the first and second hinge lines being located below the respective first and second protective strips relative to the vertical axis of the article.

DESCRIPTION OF THE INVENTION

Figure 1:
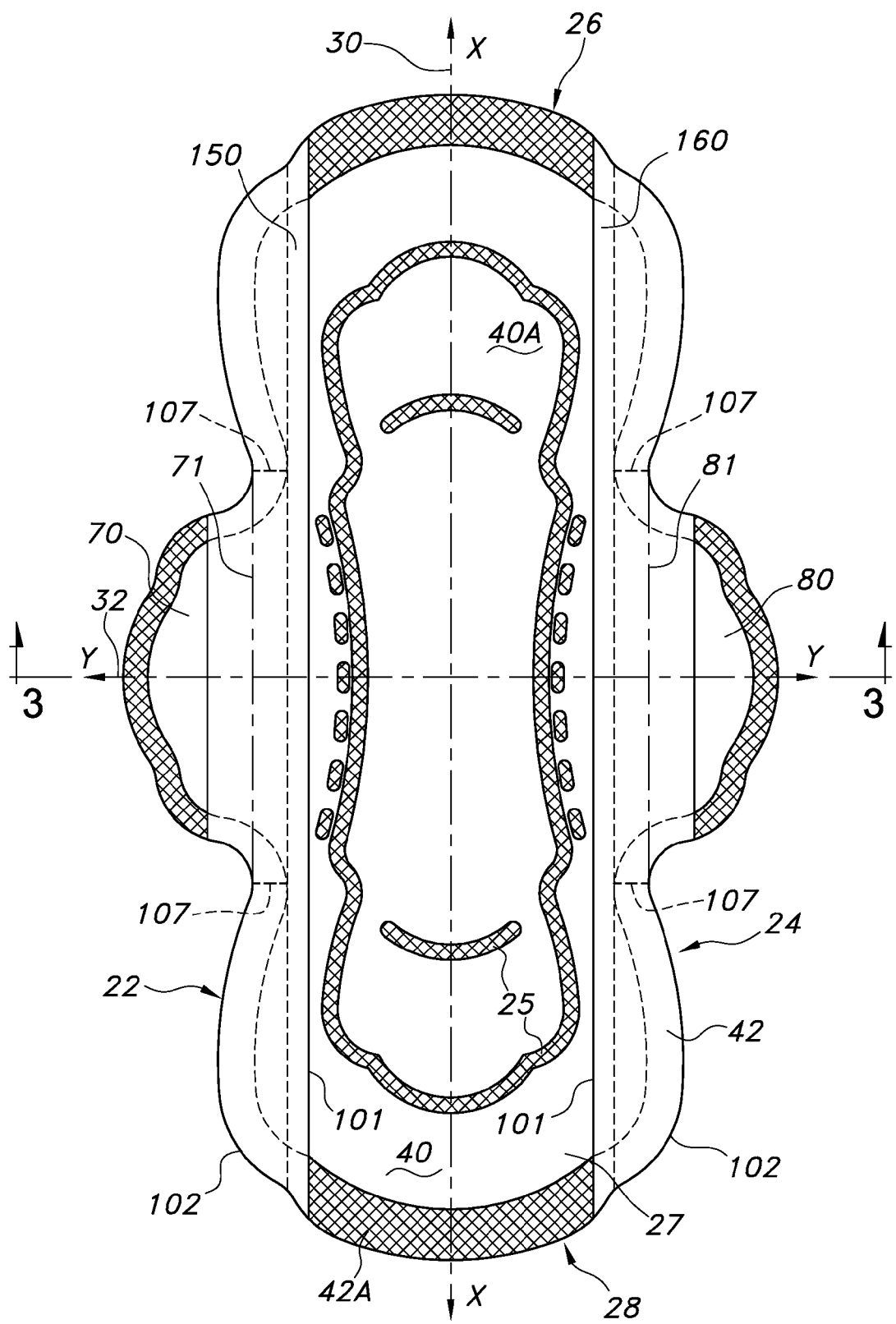
FIG. 1 is a representative top plan view of one embodiment of a personal care absorbent article according to the present invention, in this case a sanitary napkin which is shown in a flat and unfolded state.

In reference to FIGS. 1, 2, 3, 4 and 6 of the drawings there is shown an absorbent personal care articles in a flat and unfolded state. Except as otherwise noted, discussion of dimensions of the article and/or the positions of individual components thereof are in reference to the article being in a flat and unfolded state and further, in the event elasticated components are utilized, dimensions are in reference to the article being in an uncontracted state. Further, as used herein, the terms "comprising" or "including" are inclusive or open-ended and do not exclude additional unrecited elements, compositional components, or method steps. Accordingly, the terms "comprising" or "including" encompass the more restrictive terms "consisting essentially of" and "consisting of."

In reference to FIGS. 1, 2, 3, 4 and 6, an absorbent personal care article 20 is provided comprising a liquid permeable topsheet 40, a liquid impermeable backsheet 50 and an absorbent core 60. The absorbent article 20 has a lengthwise or longitudinal direction and X axis 30, a widthwise or transverse direction and Y axis 32 and a vertical direction and Z axis 34 normal to the plane defined by the X and Y axes. The longitudinal centerline of the article 20 is also represented by the X axis 30 and the transverse centerline is represented by the Y axis 32. The absorbent article 20 can comprise any one of numerous elongate shapes including, but not limited to, triangular, rectangular, dog-bone and elliptical. In addition, it will often times be desirable for the article to have rounded corners and/or generally convex ends. The article 20 defines opposed first 22 and second 24 longitudinal sides and opposed front 26 an rear 28 ends.

The absorbent article 20 desirably has a length between about 80 millimeters (mm) and about 450 mm, and still more desirably a length between about 150 mm to about 290 mm. The absorbent article 20 desirably has a maximum width (excluding the wings) between about 40 and about 160 mm, and still more desirably a maximum width between about 51 mm and about 95 mm.

Figure 6:
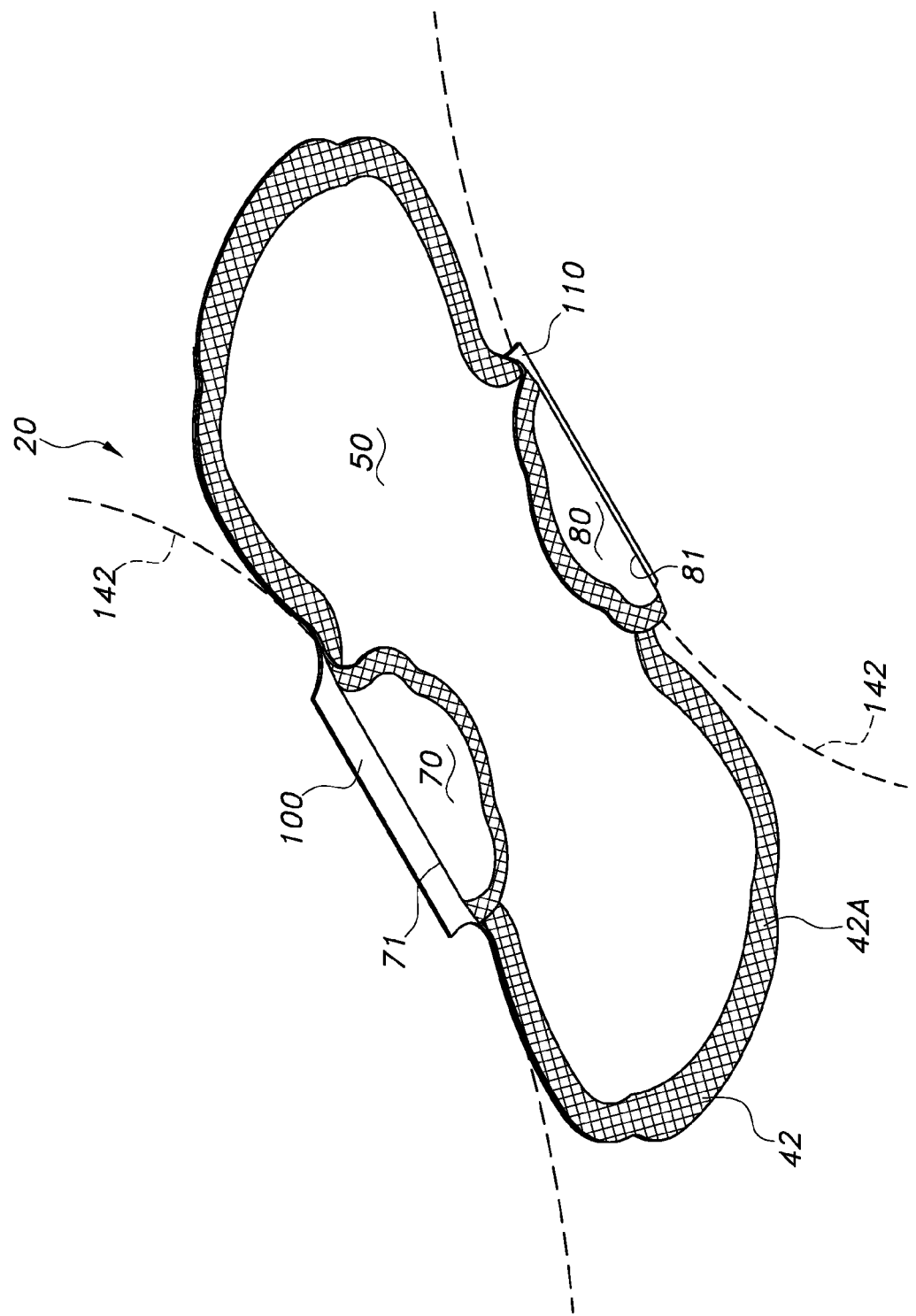
FIG. 6 is a perspective bottom view of an article of the present invention showing the wings folded over onto the backsheet of the article thereby exposing the underside of the protective strips.

The absorbent article 20 further includes a first wing or flap 70 and second wing or flap 80 extending from opposite longitudinal sides 22 and 24 of the article 20. Each of the wings has a wing proximal edge 72, 82 and a wing distal edge 74, 84. The first and second wings 70, 80 desirably extend from about 20% to about 75% of the length of the article 20. In a further aspect, the wings desirably have a length, in the longitudinal direction X, of from about 40 mm to about 160 mm, and still more desirably a length from about 80 mm to about 100 mm. The wings 70 and 80 are designed to each be folded downwardly along a hinge line 71 and 81 so they can be secured to the underside of a wearer's undergarment or to one another. See FIGS. 1 and 6. In FIG. 6, the outline of the edge of a representative undergarment is represented by dashed line 142. Where these hinge lines fall will sometimes depend on the shape and width of the undergarment to which they are being attached or wrapped around.

The wings can be positioned about the transverse centerline (Y axis 32) or may be positioned either some distance forward or rearward of the transverse centerline as may be desired to better accommodate the particular shape of the article and/or use on a particular style of garment. In addition, while not shown, it is noted that absorbent articles can, if desired, contain more than one set of opposed wings along the longitudinal sides of the product.

A portion of the outside or garment facing surface of the wings 70, 80 include one or more fasteners 90. See FIG. 2. The fasteners 90 will be selected to releasably engage either a garment or an overlapping portion of an opposed wing. Numerous adhesives and mechanical hook-type fasteners that releasably attach to one another or a user's garments are well known in the art and are suitable for use in connection with the present invention. Pressure sensitive adhesives are particularly well suited for use with the present invention. However, in order to protect the adhesive from contamination or drying prior to use, the adhesive is commonly protected by one or more releasable peel strips 92 as are known in the art. A suitable releasable peel strip is a white Kraft paper having a silicone coating on one side so that it can be easily released from the adhesive. In addition, with respect to wing-to-wing attachment, examples of specific mechanical hook, adhesive and other fastening systems include but are not limited to those described in WO03/015682 to Hammonds et al.; WO03/015684 to Hammonds et al. and US2004013317 to Steger et al.

The shape of each wing 70, 80 can be symmetrical or asymmetrical as desired. For example, in the embodiments shown in FIGS. 1, 2, 4 and 6, the wings are symmetrical and symmetrical about the transverse centerline 32. This is typically desirable when the absorbent core 60 is likewise symmetrical about the transverse centerline 32. In an alternate embodiment (not shown), the absorbent core 60 can be shaped to have a wider front and a narrower rear section in order to better conform to a tanga or thong type undergarment as well as a wider rear and a narrower front section for use in connection with certain overnight feminine hygiene product designs. In such designs, which are widely available, pairs of wings can be used on either side of the article 20. When this is the case, the article 20 will have a front and a rear wing (not shown) on each side of the article. In this type of configuration, the pairs of wings on each side of the article can be centered about the transverse centerline 32 and/or shifted to a greater or lesser degree either forwardly or rearwardly relative to the transverse centerline.

With respect to the general function and composition of the article 20, the backsheet or outer cover 50 functions to isolate absorbed fluids from the wearer's garments and therefore comprises a liquid-impervious material. In one aspect the backsheet 50 may optionally comprise a material that prevents the passage of liquids but allows air and water-vapor to pass there-through. The backsheet 50 can comprise a single layer or multiple layers and these one or more layers can themselves comprise similar or different materials. Suitable backsheet materials include, but are not limited to, polyolefin films, nonwovens and film/nonwoven laminates. The particular structure and composition of the backsheet may be selected from various known films and/or fabrics with the particular material being selected as appropriate to provide the desired level of liquid barrier, strength, abrasion resistance, tactile properties, aesthetics and so forth. Suitable backsheets include, but are not limited to, those described in U.S. Pat. No. 4,578,069 to Whitehead et al.; U.S. Pat. No.

4,376,799 to Tusim et al.; U.S. Pat. No. 5,695,849 to Shawver et al; U.S. Pat. No. 6,075,179 et al. to McCormack et al. and U.S. Pat. No. 6,376,095 to Cheung et al.

The topsheet 40 functions to receive and take in fluids, such as urine or menses, and therefore comprises a liquid permeable material. Additionally, topsheets can further function to help isolate the wearer's skin from fluids held in the absorbent core 60. Topsheets 40 can comprise a single layer or multiple layers and these one or more layers can themselves comprise similar or different materials. Topsheets are well known in the art and may be manufactured from a wide variety of materials such as, for example, porous foams, reticulated foams, apertured plastic films, woven materials, nonwoven webs, apertured nonwoven webs and laminates thereof. It is also well known that one or more chemical treatments can be applied to the topsheet materials in order to improve or retard movement of the fluid through the topsheet and into the article. Suitable topsheets include, but are not limited to, those described in U.S. Pat. No. 4,397,644 to Matthews et al.; U.S. Pat. No. 4,629,643 to Curro et al.; U.S. Pat. No. 5,188,625 Van Iten et al.; U.S. Pat. No. 5,382,400 to Pike et al.; U.S. Pat. No. 5,533,991 to Kirby et al.; and U.S. Pat. No. 6,410,823 to Daley et al.

The topsheet 40 has a top surface 27 and a bottom surface 29. The topsheet 40 shown in FIGS. 1, 2, 3 and 4 is what is often referred to as a dual layer cover as it has a central portion or strip 40A straddled by two opposed lateral strips of material 40B which may be the same or different from the central portion 40A and can be joined via adhesive 40C or other securement means including, but not limited to, thermal and ultrasonic bonding. Such a two layer or dual layer cover configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. It is also contemplated that such two layer topsheet materials may additionally include elastic components (not shown) along their side edges to lift up portions of the side materials during use, thereby forming physical barriers or cupping features on the product so as to fit more closely to the body of a user.

Between the liquid pervious topsheet 40 and liquid impervious backsheet 50 is positioned an absorbent core 60. The absorbent core 60 functions to absorb and preferably "lock-up" the bodily fluids that pass into the absorbent article 20 through the topsheet 40. The absorbent core 60 can comprise a single layer or multiple layers and these one or more layers can themselves comprise similar or different materials. In order to efficiently and effectively utilize the absorbent capacity of the article 20, it is common for the absorbent core 60 to include one or more liquid distribution layers or wicking layers in combination with a highly absorbent layer that preferentially absorbs and retains the liquids. Suitable wicking layers include, but are not limited to, bonded-carded webs, hydroentangled nonwoven webs, or spunbond webs containing fibers treated with or containing one or more topical agents that improve the contact angle with the bodily fluid and/or modify the flow properties of the bodily fluid. Highly absorbent layers often include, but are not limited to, batts or webs containing wood pulp fibers, superabsorbent particles, synthetic wood pulp fibers, synthetic fibers and combinations thereof. The absorbent core 60 may comprise any one of a number of materials and structures, the particular selection of which will vary with the desired loading capacity, flexibility, body fluid to be absorbed and other factors known to those skilled in the art. By way of example, suitable materials and/or structures for the absorbent core include, but are not limited to, those described in U.S. Pat. No. 4,610,678 to Weisman et al.; U.S. Pat. No. 6,060,636 to Yahiaoui et al.; U.S. Pat. No. 6,610,903 to Latimer et al.; US20100174260 to Di Luccio et al.; and U.S. Pat. No. 7,358,282 to Krueger et al.

The shape of the absorbent core 60 can vary as desired and can comprise any one of various shapes including, but not limited to, generally triangular, rectangular, dog-bone, elliptical and asymmetrical shapes. Asymmetrical shapes wherein the back or rear portion or the article 60 is larger than the front portion are commonly used in articles that are designed for overnight usage where larger capacity and storage are required. In one embodiment, the absorbent core 60 has a shape that generally corresponds with the overall shape of the article 20 such that the absorbent core 60 terminates proximate the edge seal 42 and wings 70, 80. The dimensions of the absorbent core 60 can be substantially similar to those referenced above with respect to the absorbent article 20; however it will be appreciated that the dimensions of the absorbent core 60 while similar will often be slightly less than those of the overall absorbent article 20 in order to be contained therein.

As previously indicated, the absorbent core 60 is positioned between the topsheet 40 and backsheet 50. The individual layers comprising the article 20 optionally can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. In one embodiment, and in reference to FIG. 1, the absorbent core 60 can be sealed between the topsheet 40 and backsheet 60 along the perimeter of the absorbent core 60 along edge seal 42 formed by the application of heat and pressure to melt thermoplastic polymers located in the topsheet 40 and/or backsheet 50, alternatively the seal 42 can be formed by adhesive or combinations of adhesives, heat and pressure. For example, all or a portion of the seal 42 may comprise a thermal bond using a calendered bond pattern such as the cross-hatch bond pattern 42A. See FIGS. 1 and 6. For example, the seal 42A may extend around the entire periphery of the article 20 or only around select portions such as, for example, the front end 26, rear end 28 and the wing distal edges 74 and 84. Further, the cross-hatch bond pattern 42A is illustrative only and it should be understood that other embossing patterns are also permissible.

To further assist in fluid handling one or more optional layers (not shown) may be used between the topsheet 40 and the absorbent core 60 and, if desired, between the absorbent core 60 and the backsheet 50. In addition, the absorbent core 60 may be wrapped with what is commonly referred to as a core wrap (not shown) such as a tissue wrap, a nonwoven layer of fibrous meltblown nonwoven, or a combination of spunbond and meltblown fibrous nonwoven web materials.

The wings 70 and 80 can be constructed from materials described above with respect to the topsheet 60 and backsheet 50. In one embodiment, such as is shown in cross-section in FIG. 3, the wings 70 and 80 can comprise an extension of the layers of material forming the topsheet 40 and/or the backsheet 50 and they can be welded together along edge seal 42A. In addition, their inner surfaces can be adhered to one another by, as for example, a layer of adhesive 40C similar to that used to join the portions 40A and 40B of topsheet 40. Such wings can be integrally formed with the main portion of the absorbent article 20. Alternatively, the wings 70 and 80 can be formed independently and separately attached to an intermediate section of the article 20. Wings 70 and 80 that are made independent of the other components of the absorbent article 20 can be welded onto or adhesively joined to a portion of the topsheet 40 and/or backsheet 50. In addition, as is known in the art, when cutting materials to the desired shape it is preferable to arrange the components so as to minimize waste. Examples of processes for manufacturing absorbent articles and wings include, but are not limited to those described in U.S. Pat. No. 4,059,114 to Richards; U.S. Pat. No. 4,862,574 to Hassim et al. WO1997040804 to Emenaker et al.; U.S. Pat. No. 5,342,647 to Heindel et al.; US20040040650 to Venturino et al.; and U.S. Pat. No. 7,070,672 to Alcantara et al.

In order to further assist with the maintenance of the article 20 in the desired location on the undergarment, garment adhesive 94 or other attachment means may be applied to the garment facing side of the backsheet 50. To protect the garment adhesives 94 prior to use, peel strips 96 may be releasably adhered to the garment facing side of the adhesives which can then be removed prior to use and installation of the article 20 in the wearer's undergarment (not shown). The use of garment adhesive 94 on the backsheet 50 to help secure placement of an absorbent article 20 on the garment is well known in the art and there are numerous adhesive patterns and releasable peel strips suitable for use with the present invention. Examples of suitable garment adhesives, patterns and release sheets include, but are not limited to, those described in DE700225U1; U.S. Pat. No. 3,881,490 to Whitehead et al.; U.S. Pat. No. 3,913,580 Ginocchio; U.S. Pat. No. 4,337,772 to Roeder et al.; GB1349962 Roeder; U.S. Pat. No. 4,556,146 to Swanson et al.; and US20070073255A1 to Thomas et al.

The absorbent articles of the present invention may further include one or more components or elements as may be desired. By way of example, the absorbent article 20 may optionally include slits, voids or embossing on the topsheet and/or absorbent core in order to improve fluid intake, fluid distribution, stiffness (bending resistance) and/or aesthetic appeal. As a specific example and in reference to FIGS. 1, 2, 3 and 4, embossing 25 can extend into both the topsheet 40 and absorbent core 60 as well as intermediate layers. Examples of additional suitable embossing patterns and methods include, but are not limited to, those described in U.S. Pat. No. 4,781,710 Megison et al.; EP769284A1 to Mizutani et al.; US20050182374 to Zander et al.; and U.S. Pat. No. 7,686,790 to Rasmussen et al.

In order to facilitate leakage protection along the first side 22 and second side 24 of the article 20, the article is equipped with pieces of material which form protective strips whose function it is to remain more generally in the plane defined by the X and Y axes when the wings 70 and 80 are folded under to secure the article 20 to the wearer's undergarment. Referring to FIGS. 1, 2, 3 and 4, the first protective strip 100 and the second protective strip 110 each define a proximal edge 101 and distal edge 102 with a width 103 therebetween. The first and second protective strips 100, 110 each define a respective front end portion 104, a rear end portion 106 and a mid-portion 108 disposed between the front end portion 104 and the rear end portion 106. The front end portions 104 are each respectively separated from the mid-portions 108 by a front transition portion 105 while each rear end portion 106 is separated from its respective mid-portion 108 by a rear transition portion 109.

The distal edges 102 can be divided into a front portion distal edge 102A, a rear portion distal edge 102B and a mid-portion distal edge 102C. The front portion distal edge 102A and the mid-portion distal edge 102C are separated by a front transition portion distal edge 102D while the rear portion distal edge 102B and the mid-portion distal edge 102C are separated by a rear transition portion distal edge 102E. The proximal edges 101 of the first and second protective strips 100 and 110 are shown as being linear or straight as are the mid-portion distal edges 102C and thus, they are parallel to one another. Alternatively the edges can be generally parallel meaning that the respective edges are within ten degrees of being parallel to one another. In other embodiments the proximal edge can be non-straight if desired. In contrast, the respective front portion distal edges 102A of the front end portions 104 and the rear portion distal edges 102B of the rear end portions 106 are non-linear as are the distal edges 102D of the front transition portions 105 and the distal edges 102E of the rear transition portions 109. Specifically, the respective distal edges 102A and 102B of the front end portions 104 and rear end portions 106 are generally convex in relationship to the proximal edges 101 while the distal edges 102D of the front transition portions 105 and the distal edges 102E of the rear transition portions 109 are generally concave relative to the proximal edges 101.

Figure 4:
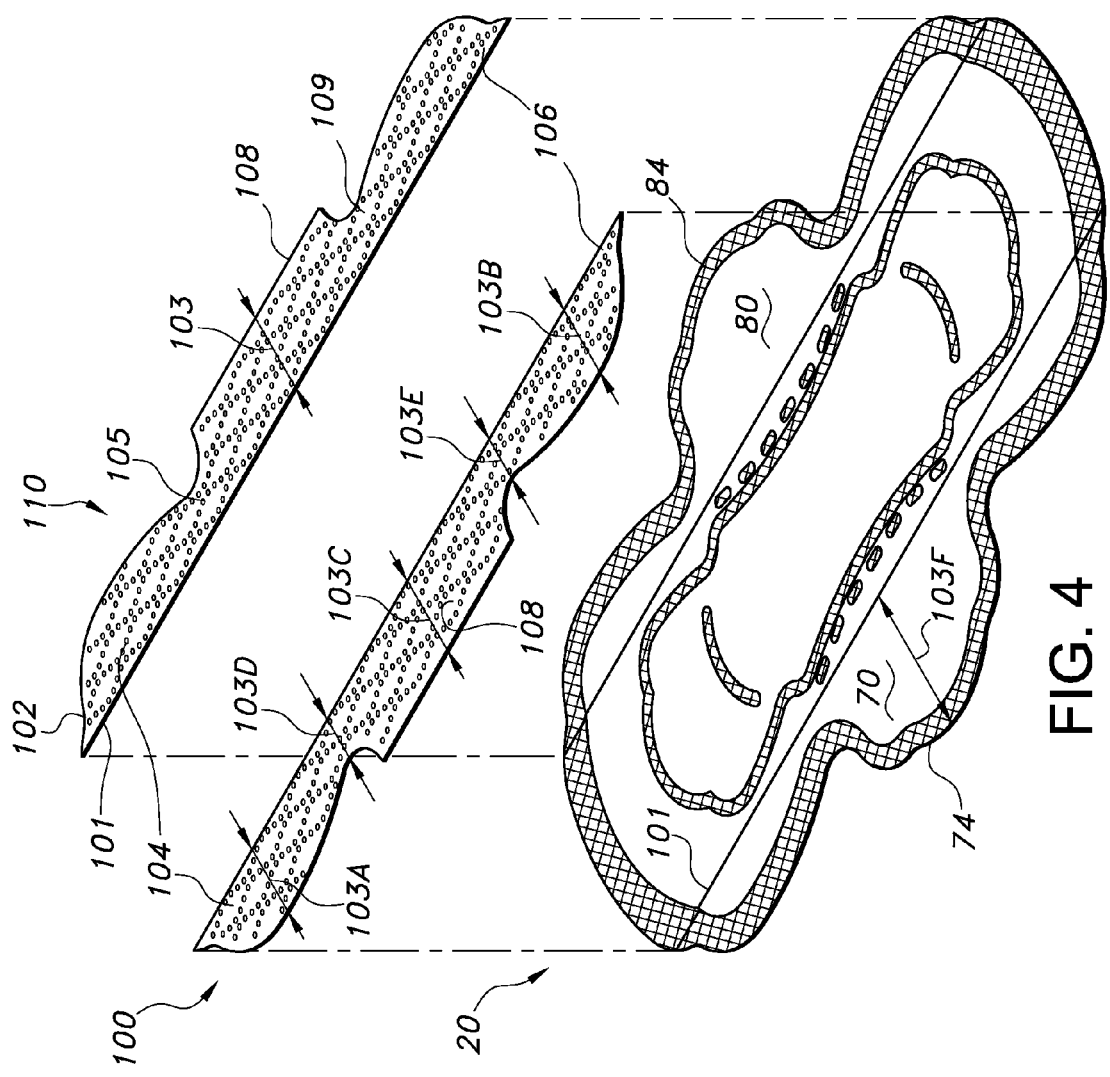
FIG. 4 is an exploded perspective view of the article of the present invention in FIG. 3.

The widths 103 of the first and second protective strips 100 and 110 will vary as can be seen in FIGS. 1, 2, 4 and 5. By "width" it is meant a measurement in the direction of the transverse axis Y. Referring to FIG. 4, in some applications, the first protective strip 100 and the second protective strip 110 will each have a mid-portion width 103C which is generally equal to either or both of the respective front portion widths 103A and the respective rear portion widths 103B. By generally equal it is meant that the widths (as measured by their greatest values perpendicular to the proximal edges of the strips) of comparative sections are within about ten percent of one another. In other and more preferred executions, the mid-portion width 103C will be greater than the front portion width 103A and rear portion width 103B. For most configurations of the article 20 these widths of the front, rear and mid-portions will range between about 5 mm and about 25 mm, and more particularly between about 15 mm and about 22 mm.

The front transition widths 103D of the respective front transitions portions 105 will be less than the widths of the front portions 103A and the mid-portions 103C. Similarly, the rear transition widths 103E of the respective rear transitions portions 106 will be less than the widths of the rear portions 103B and the mid-portions 103C. For most configurations of the article 20 these widths of the transition-portions 103D and 103E will range between about 5 mm and about 22 mm, and more particularly between about 10 mm and about 15 mm. Again such comparisons are made using the maximum widths in the respective portions measured normal to the proximal edges of the strips.

One of the advantages of the present design is that the protection provided by the protective strips 100 and 110 can be accomplished without expanding the overall dimensions of the article 20. As can be seen from, for example, FIGS. 1, 2 and 4 the protective strips 100 and 110 do not extend beyond either the overall length or width of the article 20 as the distal edges 102 of the strips 100 and 110 do not extend beyond the lateral or longitudinal dimensions of the overall product and the sides 22 and 24 and the end 26 and 28 of the article 20. The front and rear end portions 104 and 106 have distal edges which are in vertical alignment with the edges of the underlying product and thus do not extend beyond the first side edge 22 and the second side edge 24. Furthermore, the mid-portions 108 of the strips 100 and 110 do not extend beyond the lateral edges of the respective wings 70 and 80 when the product is in a flattened state as shown in the drawings. Generally, the maximum width of the mid-portion 103C will be less than the maximum width of the wings 70 and 80 as denoted by reference numeral 103F which is the distance between the proximal edge 101 and the wing distal edge 74, 84. In making this determination, the proximal edge 101 should be used as the reference point for both distal measurements. More desirably, the maximum width of the mid-portion 103C will be between about 20 and about 60 percent of the maximum width 103F of the wings 70 and 80 and more preferably between about 30 and about 50 percent and alternatively between about 20 and about 40 percent or between about 40 and about 60 percent.

To maintain good side leakage protection, it is also desirable that the mid-portion distal edge 102C extend an adequate distance beyond the hinge lines 71 and 81 of the wings 70 and 80 such that when the wings 70 and 80 are folded downwardly as shown in FIG. 6, the protective strips 100 and 110 will still be exposed and remain generally in the plane created by the longitudinal and transverse axes X and Y. As a result, it is desirable that the mid-portion distal edge 102C extend between about 1 and about 20 millimeters beyond the respective hinge lines 71 and 81 of the wings 70 and 80 and more preferably between about 5 and about 15 mm beyond the respective hinge lines 71 and 81 of the wings 70 and 80.

Figure 5:
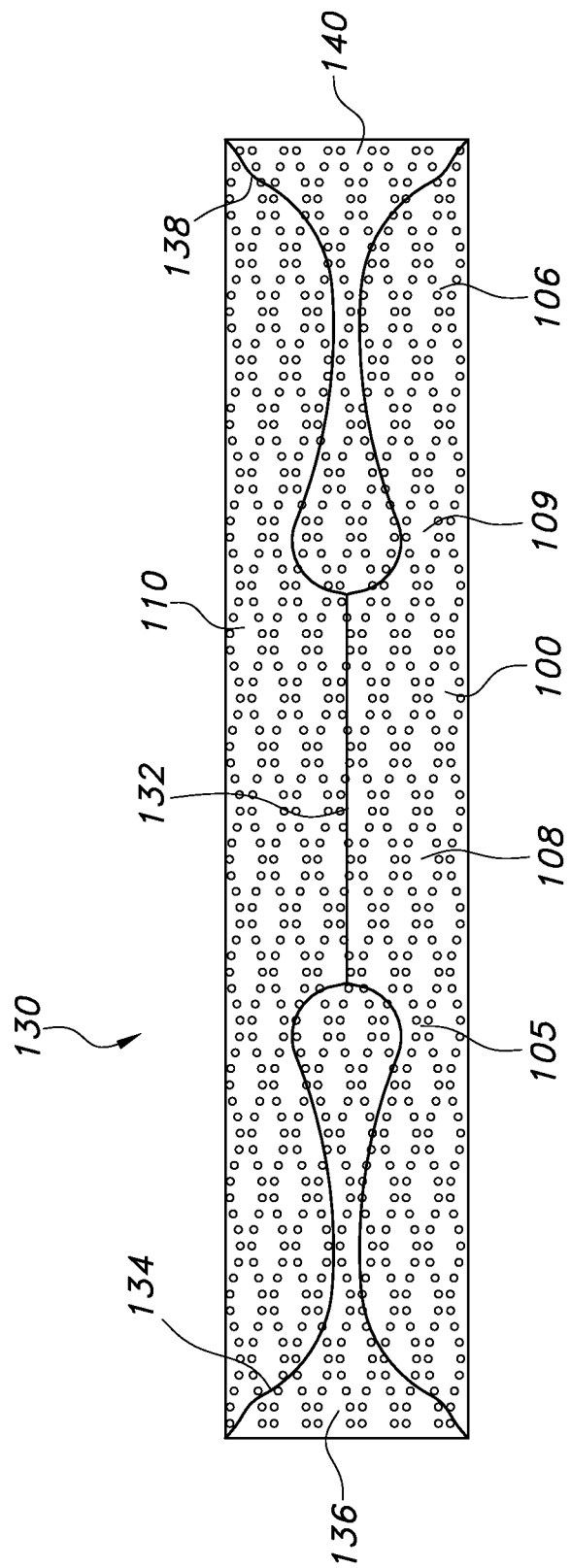
FIG. 5 is a top plan view of a protective strip of the present invention and the cut-out pattern for forming a pair of such strips from a single piece of material.

Referring to FIG. 5, in order to maximize the cost-effectiveness of forming the first protective strip 100 and the second protective strip 110, they may be formed from a single sheet of material 130. As shown in FIG. 5, the mid-portions 108 have a common cut line 132 while the respective front end portions 104 and front transition portions 105 can be formed from a single front cut line 134 which results in a front waste piece 136. Similarly, the respective rear end portions 106 and rear transition portions 109 can be formed from a single rear cut line 138 which results in a rear waste piece 140. Once the first protective strip 100 and the second protective strip 110 have been cut, they can be inverted and secured in place on the article 20.

One of the key aspects of the present invention is the fact that the protective strips 100 and 110 are stiffer than the first and second flaps or wings 70 and 80. The stiffness of the strips can be affected in a number of ways. First is the material chosen to make the strips. It is generally desirable that the strips be soft to the touch as they will be in contact with the skin of the wearer of the article 20. The protective strips 100 and 110 can be made from a wide variety of materials including the same materials used to make the topsheet 40, the backsheet 50 and the wings 70 and 80. They can be made from fibrous nonwoven webs such as, for example, spunlace, airlaid materials such as through air bonded carded webs, chemically bonded carded webs, thermally bonded carded webs, spunbond webs and meltblown webs as well as films and laminates of the foregoing materials. The strips may also be formed of laminates wherein the outer body-contacting surfaces are made from softer materials while the inner layer or layers are made from stiffer materials. In addition, other materials such as films, scrims, netting and other materials may be used alone or in combination with the other materials listed herein to yield a strip of material that is both soft and sufficiently stiff so as to resist bending during use. Furthermore, they may be treated to be more or less hydrophilic or hydrophobic. Generally the basis weight of the protective strips will range between about 15 and about 200 grams per square meter (gsm), more preferably between about 20 and about 50 gsm. It is also preferable that the material used to form the protective strips not be elastic or extensible.

Generally it is desirable that the strips 100 and 110 have a stiffness of between about 1.0 and about 10.0 grams force and more desirably between about 2.5 and about 6.3 grams force. When comparing the stiffness of the strips 100 and 110) to the stiffness of the first and second wings (70 and 80) it is generally desirable that the strips have a stiffness value that is at least about 20 percent greater than the stiffness of the first and second wings by themselves desirably at least about 50 percent and more desirably at least about 100 percent.

Figure 2:
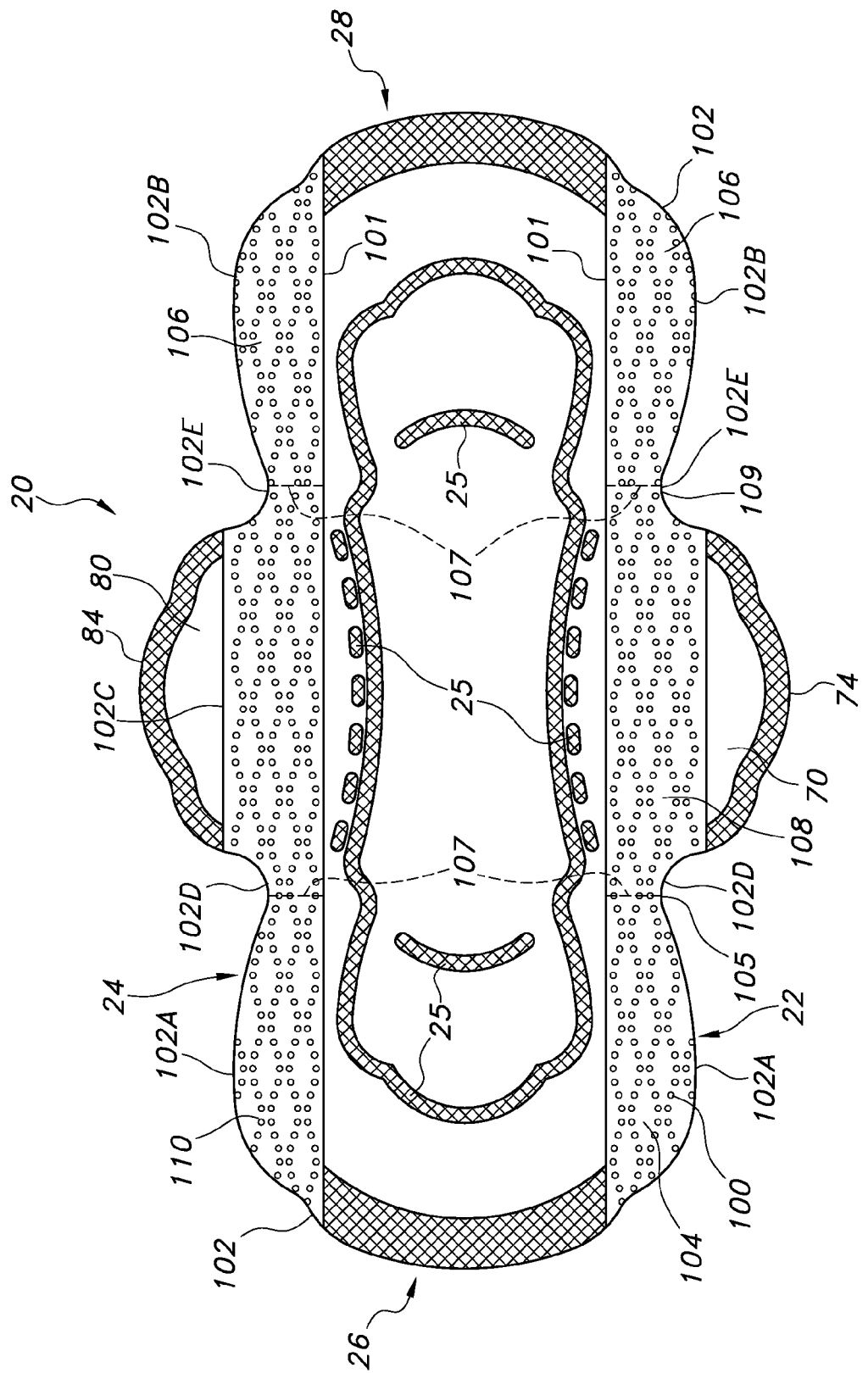
FIG. 2 is a representative top plan view of another embodiment of a personal care absorbent article of the present invention in a flat and unfolded state.

Additional processing steps can be taken to further improve the stiffness of the strips 70 and 80. Referring to FIGS. 2, 4 and 5, it can be seen that the strips 100 and 110 are embossed with a series of sinusoidal point embossments the purpose of which is to compress the material(s) forming the strips and increase the overall stiffness of the material. Such embossments can be made using patterned rollers preferably which are heated so as to melt and partially bond the materials/fibers together. It should also be understood that the embossing pattern shown in the referenced drawings are for illustration purposes only and that other embossing patterns and techniques may be utilized with the present invention. For example, ultrasonic bonding may also be used as well as solid lines of embossing that can run parallel to either or both the longitudinal axis X and the transverse axis Y as well as at angles to these axes. Further, select portions of the strips 100 and 110 can be made stiffer than other portions. For example, the mid-portion 108 can be made stiffer than either or both of the front end portion 104 and rear end portion 106 and vice versa. Alternatively, select areas of a particular portion 104, 105, 106, 108 and 109 can be made stiffer than other areas of the same portion or other portions.

Further processing steps to increase the stiffness of the strips 100 and 110 can include, but are not limited to, using adhesives or other coatings such as waxes and polymer coatings on the upper and or lower sides of the strips or between layers when the strips comprise laminates of individual layers. As with the embossments, the adhesive can be laid down in the same types of patterns described with the embossing or in different patterns. Further, the adhesive method of stiffening the strips can be used in conjunction with the embossing to further stiffen the strips 100 and 110. Still further, printing of the strips 100 and 110, especially with higher viscosity inks, can be used to supplement the stiffness of the strips. Such embossing, polymer coatings, waxes, adhesives, printing inks and other stiffening techniques can be collectively referred to as stiffening means.

Figure 3:
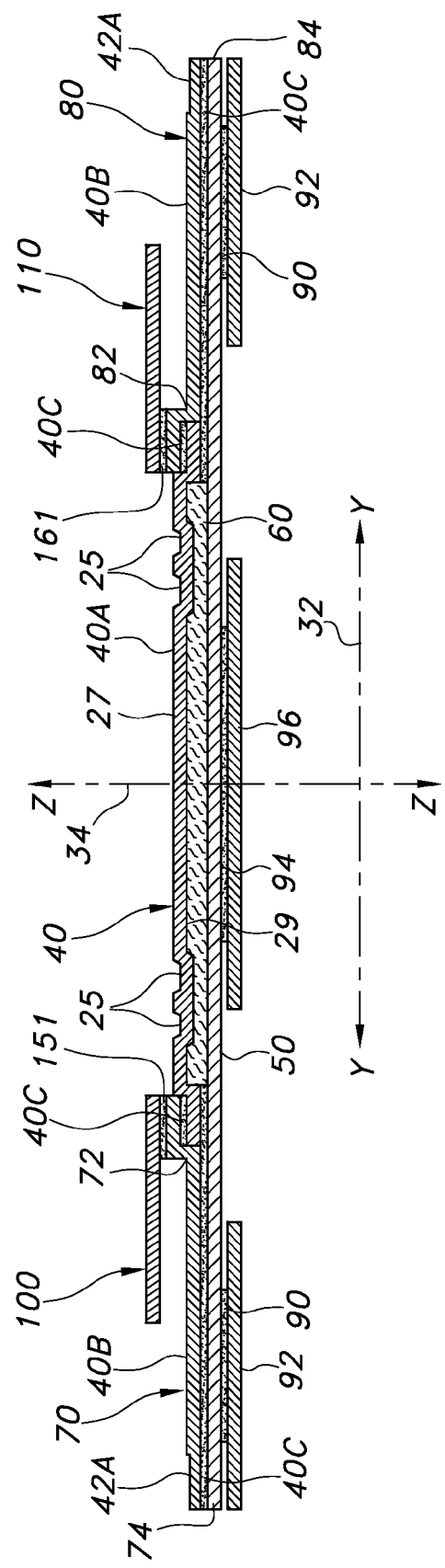
FIG. 3 is a cross-sectional side view of the article of the present invention taken along line 3-3 in FIG. 1.

Attachment of the strips 100 and 110 to the article 20 can be achieved in a number of ways. Referring to FIGS. 1, 3 and 6, the first 70 and second 80 wings are attached to or formed from the other layers of the article 20 (such as the topsheet 40 and the backsheet 50) such that each of the wings 70 and 80 preferably fold about a respective first hinge line 71 and second hinge line 81. The strips 100 and 110 should be attached to the article 20 at a location which in inboard (that is closer to the longitudinal axis X) than the hinge lines 71 and 81. See FIG. 1. As a result, when the wings 70 and 80 are folded downwardly (as shown in FIG. 6), they are free to do so as the hinge lines 71 and 81 lie below the strips 100 and 110 relative to the vertical Z axis. Consequently, when the wings 70 and 80 are folded around the edges of an undergarment (see reference numeral 142 in FIG. 6), the protective strips 100 and 110 are free to remain in an unfolded state.

Referring again to FIG. 1, the first protective strip 100 is attached to the topsheet 40 by a first attachment zone 150 and the second protective strip 110 is attached to the topsheet 40 by a second attachment zone 160 each of which can run the entire longitudinal length of the article 20. Attachment of the strips can take place using a number of means including adhesives, heat and pressure bonding, ultrasonic bonding as well combinations thereof.

Referring to FIG. 3, the respective strips 100 and 110 are each attached to the topsheet 40 by way of strips of adhesive 151 and 161. Generally these attachment zones 150 and 160 will have a width along the transverse axis Y of between about 1 and about 10 mm and more desirably between about 2 and about 6 mm. If desired, the attachment zones can be continuous in nature or discontinuous in either or both of the longitudinal and transverse directions.

As can be seen from FIGS. 1 and 3, because the strips 100 and 110 are only attached to the article 20 in the attachment zones 150 and 160, the remainder of the strips 100 and 110, including the distal edges 102 and areas of the width 103 adjacent thereto will be unattached to the article 20. In alternate embodiments (not shown), it is possible to only have the mid-portions 108 outboard of the hinge lines 71 and 81 unattached to the article 20. In such embodiments, some or all of the front end portion 104, rear end portion 106, front transition portion 105 and rear transition portion 109 can be attached to the underlying areas of the article 20.

Referring again to FIG. 3, it can be seen that the proximal edge 101 of the protective strips 100 and 110 do not overlap the absorbent core 60 when viewed along the vertical Z axis at least in the mid-portions 108 of the strips 100 and 110. As a result of this non-overlap, the overall article 20 is given a better fit and is more comfortable to wear. While this is a preferred embodiment, it is also possible for the proximal edges 101 to overlap the absorbent core 60. Furthermore, it should be appreciated that while the protective strips 100 and 110 are shown as separate pieces of material, they also may be formed from extensions of other layers of the article 20. For example, though not shown, the strips 100 and 110 may be formed from extensions of the topsheet 40. In such situations, it may be desirable to treat portions of the topsheet 40 forming the strips 100 and 110 with one or more of the aforementioned stiffening means such as, embossing, stiffening with adhesives or inks and combinations of the foregoing. If the strips 100 and 110 are made of a continuation of another layer, the strips 100 and 110 will not have actual proximal edges 101. In this case, the article 20 can be assumed to have a virtual proximal edge 101 which should be construed as an imaginary line equivalent to reference number 101 which is inboard of hinge lines 71 and 81 (that is, closer in proximity to the longitudinal centerline and X axis 30) by a distance of 5 mm as measured from the hinge lines 71 and 81. Further, in the context of the claims, in connection with such constructions without an actual proximal edge, the term "attached" and variants thereof should be construed to mean that the connection location of the strips 100 and 110 to the article 20 is the location of the imaginary line associated with reference numeral 101.

In an alternate embodiment, the protective strips 100 and 110 may be of a reduced size such that they generally only cover the mid-portion 108. See FIGS. 1 and 2. In this configuration, the protective strips may be terminated, for example, at the breakpoints 107 which are located in the front transition portions 105 and rear transition portions 109 of protective strips 100 and 110. Otherwise, all other aspects of the strips remain the same as the strips are simply devoid of the material outside of the breakpoints 107 thereby allowing the production of an article 20 with reduced material usage and therefore, reduced cost. Further, while the breakpoint 107 have been shown in the transition portions 105 and 109, it should be noted that they can be located closer or further away from the transverse axis 32 thereby increasing or decreasing the longitudinal length of the protective strips 100 and 110 and thereby increasing or decreasing their overall size and cost.

In still a further embodiment (not shown) the protective strips may be made from a portion of one of the layers, such as, for example, the lateral strips or portions 40B of the topsheet 40. As opposed to having separate sheets of material 100 and 110 which are attached to the lateral portions 40B via adhesive 40C (see FIG. 3), the adhesive 40C may be eliminated and the two layers may be substituted with a single piece of material with a fold line (not shown) in place of the adhesive 40C such that the material is folded back on itself and the fold line becomes proximal edge 101. As with other embodiments, the portion of this combined and folded material which forms the strips 100 and 110 can be acted up to increase its stiffness by using, for example, the aforementioned stiffening means such as, for example, embossing and adhesive.

Samples and Testing

The stiffness of the protective strips 100 and 110 can be measured by determining the peak load bending stiffness of the materials. This stiffness can be determined utilizing the ASTM D4032-82 CIRCULAR BEND test procedure as modified herein. This modified test is used for the purposes of the present invention and is, hereinafter, simply referred to as the "Circular Bend Procedure." The Circular Bend Procedure is a simultaneous multi-directional deformation of a material in which one face of a sample becomes concave and the other face becomes convex. The Circular Bend Procedure gives a force value related to flexure-resistance, simultaneously averaging stiffness in all directions and the values are reported as the peak load stiffness in grams force.

The plunger and plate of the apparatus in the aforementioned test procedure is modified as follows: The platform is a smooth-polished steel plate platform with dimensions of 102.0 mm by 102.0 mm by 6.35 (thickness) mm. The circular orifice measures 18.75 mm in diameter and is located in the center of the plate. The lap edge of the orifice is cut at a 45 degree angle to a depth of 4.75 mm to facilitate entry of the sample and plunger. The plunger has an overall length to the end of the ball nose of 72.2 mm, a diameter of 6.25 mm, a flat rear end, a ball nose having a radius of 2.97 mm and a needle-point which extends 0.88 mm therefrom with a 0.33 mm base diameter and a point having a radius of less than 0.5 mm. The test plate is leveled and the plunger is mounted concentrically with the orifice having equal clearance on all sides. Note that the purpose of the needlepoint is to prevent lateral movement of the test sample during testing. Therefore, if the needle-point significantly adversely affects the test sample (for example, by puncturing an inflatable structure contained within the sample), then the needle-point should not be used. The ball nose of the plunger is set well above the top of the orifice plate. From this position, the downward stroke of the ball nose of the plunger is to the exact bottom of the plate orifice. An MTS Insight Electromechanical 5 kN Standard Length tensile tester from MTS Systems Corp. of Eden Prairie, Minn. or an equivalent device with a compression load cell is used to measure the bending force.

Figure 7:
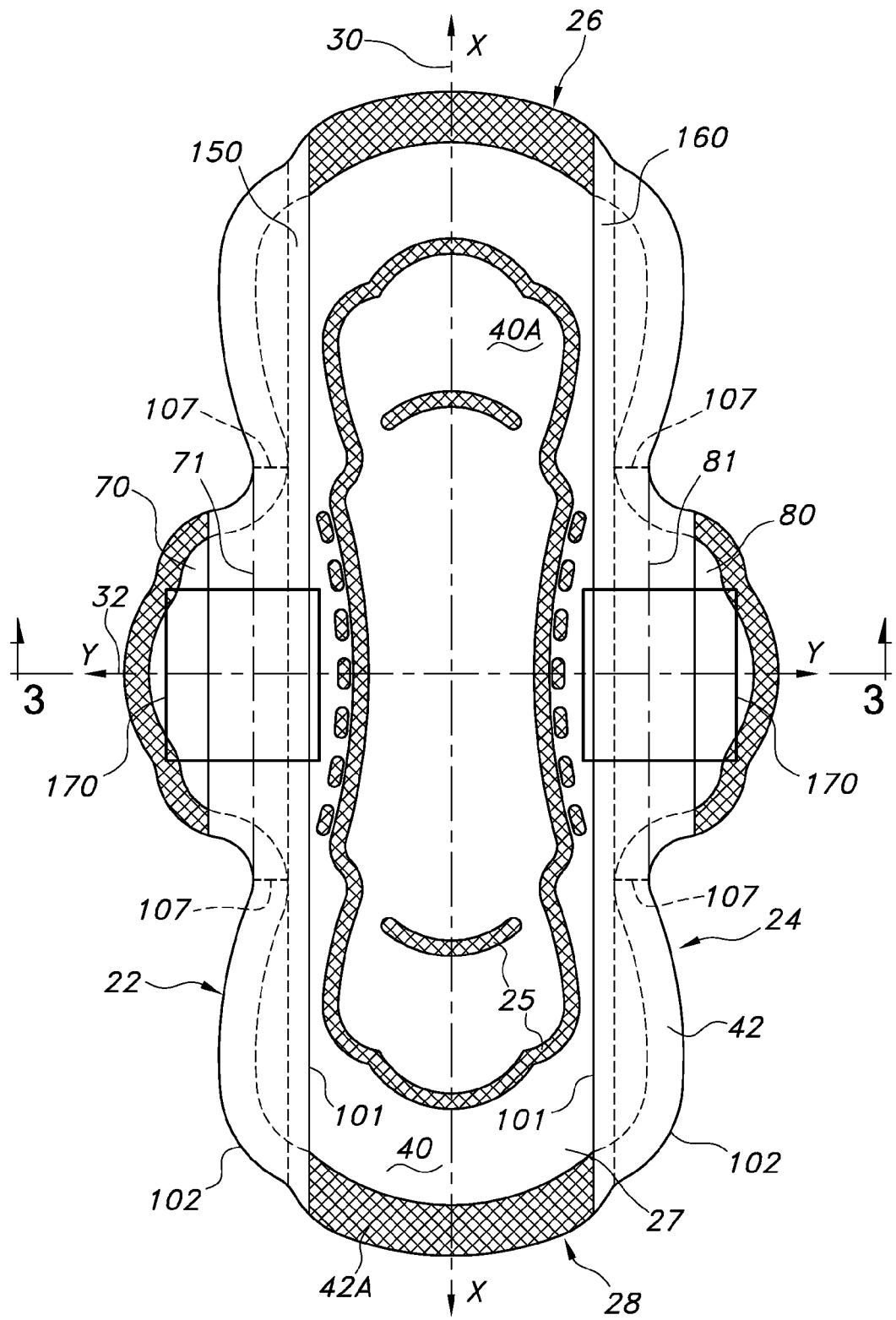
FIG. 7 is a representative top plan view of one embodiment of a personal care absorbent article according to the present invention, in this case a sanitary napkin which is shown in a flat and unfolded state. In this embodiment the location of sample cutting is illustrated.

The sample preparation procedure for the Circular Bend Procedure is as follows: Referring to FIG. 7 of the drawings, a sanitary napkin 20 is removed from any packaging that it is in and laid flat. A sample square designated 170 in FIG. 7 measuring 37.5 mm by 37.5 mm (1.47 inches by 1.47 inches) is cut form a portion of each of the wings 70, 80, preferably along the transverse center line of each wing. The cut samples are then conditioned in a room at 21.0+/−0.1 degrees Centigrade and 50.0+/−0.2 percent Relative Humidity for a period of two hours. After cutting, the sample should not be bent, folded, compressed, or otherwise deformed before being placed on the platform for testing.

The measurement procedure for the Circular Bend Procedure is as follows. The plunger speed is set at 50.0 centimeters per minute per full stroke length. A sample 170 is centered on the orifice platform below the plunger such that the topsheet 40 of the sample is facing the plunger and the backsheet 50 of the sample is facing the platform. Prior to placing the sample on the platform, the peel strip 92 if present is removed from any adhesive 90 on the garment surface of the sample and the adhesive 90 is blocked by coating it with corn starch, talc or any other suitable composition to eliminate the adhesive tack. Unnecessary touching the sample during the test should be avoided. The maximum force reading to the nearest 0.1 gram force is recorded and reported as the peak load stiffness.

Once the test of a sample has been completed, the protective strip is removed from the sample and the sample is tested again. When removing the protective strip, care should be taken not to damage the remainder of the sample. With the protective strip 100/110 removed, the second measurement of the stiffness of the sample without the protective strip 100 is taken in the same manner as described above. The contact point of the plunger for both measurements (with and without the protective strip 100/110) should be in the same position on both samples. The difference in the two stiffness measurements (with and without the protective strip) is the stiffness of the protective strip 100/110.

To determine the stiffness of the protective strips 100, 110 a series of samples were prepared and tested. Because lab samples were being prepared, sanitary napkins of the shape and design shown in FIG. 2 were prepared with and without protective strips and so the strip removal step did not have to be performed. The wings 70 and 80 were comprised of topsheet material 40B and backsheet material 50. The topsheet material was a 30 gram per square meter through air bonded carded web (TABCW) utilizing polyethylene sheath/polypropylene core bicomponent 1.5 denier staple fibers. The backsheet was polyethylene film having a basis weight of 24 gsm and a thickness of 0.03 mm. The two layers were adhesively laminated together using approximately 28 gsm of hot melt adhesive. In the samples with a protective strip, the strip was attached to the top surface of the wing and was made from a 40 gram per square meter TABW web utilizing polyethylene sheath/polypropylene core bicomponent 2.0 denier staple fibers. The protective strip was embossed with an embossing pattern such as is shown in FIG. 2. Its proximal edge 101 was attached to the topsheet 40B with a 4 mm wide strip of hot melt adhesive at and add-on of approximately 41 gsm.

Samples were cut from both wings 100 and 110 in the manner described above and testing for peak load stiffness was determined for each sample. The peak load stiffness of the strips is calculated by subtracting the peak load value for a sample without the protective strip (B) from the peak load value for the same sample with the protective strip (A). The percent increase in stiffness in the samples with protective strips as compared to samples without protective strips was calculated using the equation [(A−B)/B]×100=% increase. In evaluating products, if either protection strip has a prescribed percent increase value that falls within a claim limitation, then the product as a whole is considered to have this value even if the other protection strip of the same product is lower. The values obtained for the samples tested are set forth in Table 1 below. As each sample product has two wings, each product is denoted as having an "a" sample and a "b" sample.

TABLE 1

| Sample | Peak Load Stiffness With Protective Strip (grams force) A | Peak Load Stiffness Without Protective Strip (grams force) B | Protective Strip Peak Load Stiffness (A − B) (grams force) | % Increase in Stiffness [(A − B)/B] × 100 |
|---|---|---|---|---|
| 1a | 8.3 | 3.1 | 5.2 | 68 |
| 1b | 9.6 | 4.3 | 5.3 | 123 |
| 2a | 8.5 | 4.4 | 4.1 | 93 |
| 2b | 7.0 | 3.3 | 3.7 | 112 |
| 3a | 7.4 | 4.9 | 2.5 | 51 |
| 3b | 8.8 | 4.1 | 4.7 | 115 |
| 4a | 9.1 | 2.8 | 6.3 | 225 |
| 4b | 8.4 | 3.4 | 5.0 | 147 |
| 5a | 8.9 | 3.4 | 5.5 | 157 |
| 5b | 10.0 | 4.1 | 5.9 | 144 |
| Ave | 8.6 | 3.8 | 4.8 | 126 |

Generally it has been found that side leakage protection with the designs disclosed herein give improved results when the percent increase in peak load stiffness is at least about 20 percent, desirably at least about 50 percent and more desirably at least about 100 percent and should range between about 20 percent and about 260 percent, desirably between about 20 and about 160 percent and more desirably between about 50 and about 160 percent. The protective strip peak load will desirably range between about 1.0 and about 10.0 grams force and more desirably between about 2.5 grams force and about 6.3 grams force though values outside this range may also be used depending upon the particular end use requirements. If the protective strips are made too stiff, problems can arise such as irritation to the skin of the wearer which is an undesirable attribute.

The personal care articles can, optionally, contain one or more additional elements or components as are known and used in the art including, but not limited to, the use of fold lines, individual wrappers, elasticated flaps that extend above the plane of the topsheet in use, additional independent wings such as about the ends, odor control agents, perfumes, and the use of ink printing on one or more surfaces of the topsheet, backsheet, wings, absorbent core and other layers. Still further additional features and various constructions are known in the art. Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

What is claimed is:

1. An absorbent personal care article comprising:
    an elongate shape defined by opposed first and second sides and opposed front and rear ends; said article defining a longitudinal axis, a transverse axis and a vertical axis normal to said longitudinal axis and said transverse axis;
    a liquid permeable topsheet defining a top surface and a bottom surface, a liquid impermeable backsheet and an absorbent core disposed between said liquid permeable topsheet and said liquid impermeable backsheet;
    a first wing extending from said first side and having a wing proximal edge and a wing distal edge;
    a second wing extending from said second side and having a wing proximal edge and a wind distal edge;
    a fastener positioned on at least one of said first and second wings;

said first wing having a first hinge line and said second wing having a second hinge line, said first wing and said second wing being adapted during use to be folded along said respective first and second hinge lines downwardly relative to said vertical axis towards said backsheet;

said article further including a first protective strip and a second protective strip each defining a proximal edge and a distal edge and a width therebetween, said first and second protective strips each defining a front end portion and a rear end portion with a mid-portion disposed between said front end portion and said rear end portion, said front end portion being separated from said mid-portion by a front transition portion, said rear end portion being separated from said mid-portion by a rear transition portion;

said first protective strip being located adjacent said first side of said article and said second protective strip being located adjacent said second side of said article such that at least a portion of said first protective strip including at least a portion of said distal edge extends beyond said first hinge line and at least a portion of said second protective strip including at least a portion of said distal edge extends beyond said second hinge line, said first and second hinge lines being located below said respective first and second protective strips relative to said vertical axis;

said mid-portion of said first and second protective strips each having a distal edge at least a portion of which is straight, said front transition portion and said rear transition portion each having a width which is less than the width of said front end portion, said mid-portion and said rear end portion; and wherein said distal edge of said first and second protective strips is unattached to said article.

2. The absorbent personal care article of claim 1 wherein at least one of said front end portion and said rear end portion of said first and second protective strips is non-linear.

3. The absorbent personal care article of claim 1 wherein said first and second protective strips are embossed.

4. The absorbent personal care article of claim 1 wherein each of said first and second protective strips is attached to said top surface of said topsheet.

5. The absorbent personal care article of claim 1 wherein said distal edges of said front end portion and said rear end portion of said first and second protective strips do not extend beyond said respective first side and second side of said article.

6. The absorbent personal care article of claim 1 wherein the width of said mid-portion of said first and second protective strips is within ten percent of the width of at least one of said front end portion and said rear end portion of said respective strips.

7. The absorbent personal care article of claim 1 wherein said first and second protective strips each have a basis weight between about 15 and about 200 grams per square meter.

8. The absorbent personal care article of claim 1 wherein said distal edge of said first and second protective strips is stiffer than the remainder of said respective strips.

9. The absorbent personal care article of claim 1 wherein said first and second protective strips are attached to said article by an attachment zone.

10. The absorbent personal care article of claim 9 wherein said attachment zone is inboard of said first and second hinge lines of said respective first and second protective strips.

11. The absorbent personal care article of claim 1 wherein said proximal edge of said mid-portion of said first and second protective strips does not overlap said absorbent core.

12. The absorbent personal care article of claim 1 wherein said distal edge of said mid-portion of said first and second protective strips is unattached to said article.

13. The absorbent personal care absorbent article of claim 1 wherein, during use said article is attached to a crotch region of an undergarment, said undergarment having lateral edges, at least a portion of said protective strips extending laterally beyond said lateral edges of said undergarment.

14. The absorbent personal care absorbent article of claim 1 wherein at least a portion of said first protective strip and said second protective strip has been stiffened by a stiffening means.

15. The absorbent personal care absorbent article of claim 1 wherein said mid-portion of said protective strips individually have a peak load stiffness of between about 1.0 and about 10.0 grams force.

16. The absorbent personal care absorbent article of claim 1 wherein at least one of said first protective strip and said second has a percent increase in peak load stiffness of at least about 20 percent.

17. An absorbent personal care article comprising:

an elongate shape defined by opposed first and second sides and opposed front and rear ends; said article defining a longitudinal axis, a transverse axis and a vertical axis normal to said longitudinal axis and said transverse axis;

a liquid permeable topsheet defining a top surface and a bottom surface, a liquid impermeable backsheet and an absorbent core disposed between said liquid permeable topsheet and said liquid impermeable backsheet;

a first wing extending from said first side and having a wing proximal edge and a wing distal edge;

a second wing extending from said second side and having a wing proximal edge and a wind distal edge;

a fastener positioned on at least one of said first and second wings;

said first wing having a first hinge line and said second wing having a second hinge line, said first wing and said second wing being adapted during use to be folded along said respective first and second hinge lines downwardly relative to said vertical axis towards said backsheet;

said article further including a first protective strip and a second protective strip each defining a proximal edge and a distal edge and a width therebetween wherein at least a portion of said distal portion is straight, said first and second protective strips each being in vertical juxtaposition with said respective first wing and second wing;

said first protective strip being located adjacent said first side and said second protective strip being located adjacent said second side of said article such that at least a portion of said first protective strip including at least a portion of said distal edge extends beyond said first hinge line and at least a portion of said second protective strip including at least a portion of said distal edge extends beyond said second hinge line, said first and second hinge lines being located below said respective first and second protective strips relative to said vertical axis; and wherein said distal edge of said first and second protective strips is unattached to said article.

18. The absorbent personal care absorbent article of claim 17 wherein at least a portion of said first protective strip and said second protective strip have been stiffened by a stiffening means.

* * * * *